(12) United States Patent
Xu et al.

(10) Patent No.: US 12,327,640 B2
(45) Date of Patent: Jun. 10, 2025

(54) FINGER KNEADING RATING METHOD BASED ON INTELLIGENT MODEL PROCESSING

(71) Applicant: Jiangxi Provincial People's Hospital, Nanchang (CN)

(72) Inventors: Renshi Xu, Nanchang (CN); Xia Deng, Nanchang (CN)

(73) Assignee: Jiangxi Provincial People's Hospital, Nanchang (CN)

( * ) Notice: Subject to any disclaimer, the term of this patent is extended or adjusted under 35 U.S.C. 154(b) by 527 days.

(21) Appl. No.: 17/711,940

(22) Filed: Apr. 1, 2022

(65) Prior Publication Data
US 2023/0317280 A1    Oct. 5, 2023

(51) Int. Cl.
*G16H 50/20* (2018.01)
(52) U.S. Cl.
CPC .................... *G16H 50/20* (2018.01)
(58) Field of Classification Search
CPC .......................................... G16H 50/20
USPC ............................................. 706/12
See application file for complete search history.

(56) References Cited

U.S. PATENT DOCUMENTS

| | | | |
|---|---|---|---|
| 2017/0052074 A1* | 2/2017 | Watazu | G06F 3/00 |
| 2020/0281805 A1* | 9/2020 | Qiu | A61H 1/00 |
| 2022/0040028 A1* | 2/2022 | Song | A61H 1/0288 |

FOREIGN PATENT DOCUMENTS

CN    109330846 A  *  2/2019  ............. A61B 5/021

OTHER PUBLICATIONS https://users.ece.utexas.edu/~valvano/volume1/E-Book/C14_ADCdataAcquisition.htm, as archived Mar. 27, 2022 (Year: 2022).*

* cited by examiner

*Primary Examiner* — Austin Hicks
(74) *Attorney, Agent, or Firm* — Hemisphere Law, PLLC; Zhigang Ma

(57) ABSTRACT

Disclosed is a finger kneading rating method based on intelligent model processing. The method includes the following steps: acquiring and sending finger kneading piezoelectric data meeting a preset pressure value; receiving the piezoelectric data meeting the preset pressure value, calculating and processing the piezoelectric data by using a data model, and outputting finger effective data; receiving the finger effective data, and inputting a preset training model for training to obtain a rating model; outputting the finger effective data and displaying the finger kneading evaluation result. Through the steps above, the effective times of finger kneading could be easily obtained, and the results of inaccurate counting and scoring in a short time could be avoided, thus greatly ensuring good accuracy and reliability of the test results of this project; meanwhile, the application provides powerful evidence for early identification, early treatment and treatment detection of Parkinson's disease.

4 Claims, 2 Drawing Sheets

S100: acquiring and sending finger kneading piezoelectric data meeting a preset pressure value;

S200: receiving the piezoelectric data meeting the preset pressure value, calculating and processing the piezoelectric data by using a data model, and outputting finger effective data;

S300: receiving the finger effective data, and inputting a preset training model for training to obtain a rating model; outputting the finger effective data and displaying the finger kneading evaluation result.

FINGER KNEADING RATING METHOD BASED ON INTELLIGENT MODEL PROCESSING

TECHNICAL FIELD

The application relates to the technical field of medical treatment, and in particular to a finger kneading rating method, a device and a rating system based on intelligent model processing.

BACKGROUND

At present, there is no clinical examination plan to accurately diagnose Parkinson's disease. Only about 70%-75% of Parkinson's patients diagnosed by clinical standards are consistent with pathological diagnosis, so the specificity is not high.

The unified Parkinson's disease rating scale is widely used internationally to assess the general situation of each Parkinson's disease patient. The higher the score, the more severe the symptoms of Parkinson's disease; where the 23rd item of the third part is finger kneading. In the actual evaluation operation of finger kneading, in order to control the differences between groups and save manpower, generally these items are evaluated by an operator. For the operator, before measuring an item, the patient should be taught how to knead the thumb and forefinger with the maximum amplitude and the fastest frequency. Then in order to avoid patients' memory loss, the tester should set and observe the stopwatch, observe and count the times; eliminate unqualified kneading, and record the effective kneading times as the count number within just 5 seconds. More ratings lead to more qualitative errors, a smaller frequency and smaller amplitude.

Therefore, Parkinson's disease rating scale can't accurately confirm the degree or development process of the patient's finger kneading ability, which will lead to errors in the test of 23rd item, which will lead to errors in the third part of UPRDS score of motor function, and then lead to errors in the subsequent correlation analysis.

In addition, the collected data of Parkinson's patients are usually processed manually, which is inefficient to process a large number of collected data.

SUMMARY

The present application provides a finger kneading rating method, a device and a rating system based on intelligent model processing.

According to one aspect of the present application, a finger kneading rating method based on intelligent model processing is provided, including the following steps:

S100: acquiring and sending finger kneading piezoelectric data meeting a preset pressure value;

S200: receiving the piezoelectric data meeting the preset pressure value, calculating and processing the piezoelectric data by using a data model, and outputting finger effective data; and S300: receiving the finger effective data, and inputting a preset training model for training to obtain a rating model; outputting the finger effective data and displaying the finger kneading evaluation result.

According to another aspect of the present application, a device for realizing the above-mentioned finger kneading rating method based on intelligent model processing is provided, including:

a finger sleeve, which is used to be sleeved on fingers;

a piezoelectric converter, which is arranged on the finger sleeve to acquire and send finger kneading piezoelectric data meeting preset pressure value;

a monitor control unit (MCU), which is arranged on the finger sleeve and connected with the piezoelectric converter, and is used for receiving the piezoelectric data meeting the preset pressure value, calculating and processing the piezoelectric data by using a data model, and outputting finger effective data;

a display, which is arranged on the finger sleeve and used for receiving and displaying the finger effective data;

a battery, which is arranged on the finger sleeve and electrically connected with the piezoelectric converter, the MCU and the display.

According to another aspect of the present application, a rating system is also provided, including:

a processor;

a memory, which is used for storing processor executable instructions;

where the processor is configured to implement the finger kneading rating method based on intelligent model processing above when executing the executable instructions.

According to the application, the finger kneading rating method includes the following steps: acquiring and sending finger kneading piezoelectric data meeting a preset pressure value; receiving the piezoelectric data meeting the preset pressure value, calculating and processing the piezoelectric data by using a data model, and outputting finger effective data; receiving the finger effective data, and inputting a preset training model for training to obtain a rating model; outputting the finger effective data and displaying the finger kneading evaluation result; through the steps above, the effective times of finger kneading can be easily obtained, and the results of inaccurate counting and scoring in a short time could be avoided, to greatly ensure good accuracy and reliability of the test results of this project; meanwhile, it provides powerful evidence for early identification, early treatment and treatment detection of Parkinson's disease. An intelligent data model is used for data processing to improve efficiency. After getting the data, training is performed to get the rating model. When the kneading data need to be evaluated later, the rating model could be used for real-time rating, which improves the intelligent application.

Other features and aspects of the present application will become apparent from the following detailed description of exemplary embodiments with reference to the accompanying figures.

BRIEF DESCRIPTION OF THE FIGURES

The accompanying figures, which are incorporated in and constitute a part of the specification, together with the specification, illustrate exemplary embodiments, features and aspects of the application and serve to explain the principles of the application.

DETAILED DESCRIPTION OF THE EMBODIMENTS

Various exemplary embodiments, features and aspects of the present application will be described in detail below with reference to the accompanying figures. In the figures, the same reference symbols of the figures refer to elements with the same or similar functions. Although various aspects of the embodiments are shown in the figures, the figures are not necessarily drawn to scale unless otherwise indicated.

Embodiment 1

Figure 1:
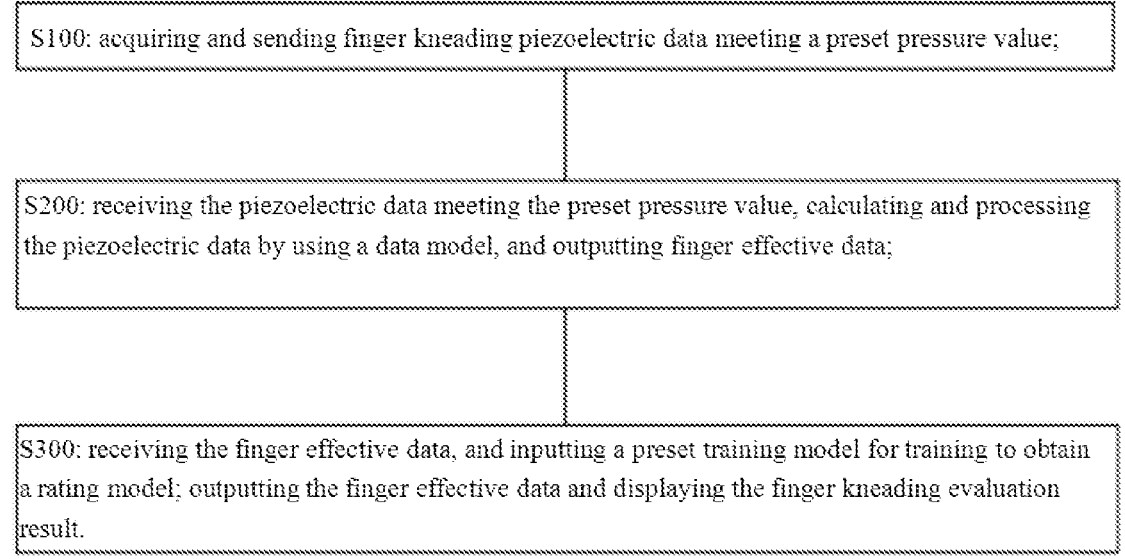
FIG. 1 is a schematic diagram of the implementation process of the finger kneading rating method based on intelligent model processing of the present application.

As shown in FIG. 1, according to one aspect of the present application, a finger kneading rating method based on intelligent model processing is provided, which includes the following steps:

S100: acquiring and sending finger kneading piezoelectric data meeting a preset pressure value; acquiring the piezoelectric data by the piezoelectric converter in contact during kneading and sent to monitor control unit (MCU) for processing, where the piezoelectric converter is arranged on the finger sleeve;

S200: receiving the piezoelectric data meeting the preset pressure value, calculating and processing the piezoelectric data by using a data model, and outputting finger effective data; using MCU to process the piezoelectric signal to obtain the pressure data during finger kneading, and judging the preset threshold and algorithm to obtain the finger effective data; and S300: receiving the finger effective data, and inputting a preset training model for training to obtain a rating model; outputting the finger effective data and displaying the finger kneading evaluation result; using the MCU to send the finger effective data to the display, and displaying the data after decoding.

In a possible implementation, optionally, in S200, receiving the piezoelectric data that meets the preset pressure value, calculating and processing the piezoelectric data by using a data model, and outputting finger effective data includes:

presetting a noise reduction algorithm, and performing noise reduction pretreatment on the piezoelectric data to obtain noise reduction data;

analyzing the noise reduction data to obtain piezoelectric pressure data; and calculating and obtaining effective pressure data according to the piezoelectric pressure data.

Piezoelectric data includes signal data that does not meet the set standard. The piezoelectric data is preprocessed by MCU preset algorithm for noise reduction. After eliminating invalid signals, the piezoelectric data is analyzed to obtain effective data sent to the display. Noise reduction algorithms and methods are not limited here.

In a possible implementation, optionally, in S200, receiving the piezoelectric data meeting the preset pressure value, calculating and processing the piezoelectric data by using a data model, and outputting finger effective data further includes:

presetting an effective pressure threshold;

comparing the piezoelectric pressure data with the effective pressure threshold, judging, obtaining and outputting the piezoelectric pressure data not lower than the effective pressure threshold.

After the piezoelectric data is denoised, it also needs to be screened to obtain the data that meets a certain pressure threshold, such as 0.05 Pa, as effective data. Piezoelectric pressure data of not less than 0.05 Pa is obtained as output finger effective data and displayed. The data accuracy is improved after two comparative screening.

In a possible implementation, optionally, in S100, acquiring and sending finger kneading piezoelectric data meeting a preset pressure value includes:

presetting arrays of finger kneading times;

according to the arrays, obtaining the finger kneading piezoelectric data of all times in each array; and calculating the average value of piezoelectric data of each array and taking as a piezoelectric data set.

When obtaining piezoelectric data during kneading, the data are obtained by arrays, and the mean values of each array are calculated separately, and each array of mean values is regarded as piezoelectric data to improve the accuracy of data collection.

The data model could be a data analysis model, which is not limited here; the training model can be a daily model.

Embodiment 2

Figure 2:
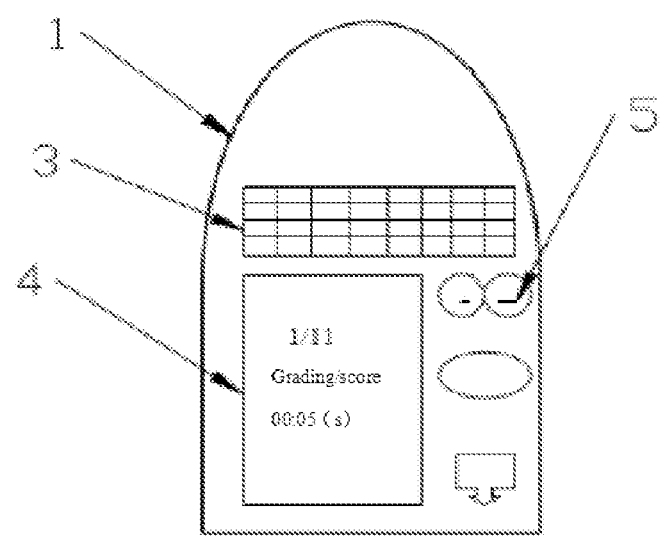
FIG. 2 is a schematic diagram showing the composition and structure of the finger kneading function rating device of the present application.
Figure 3:
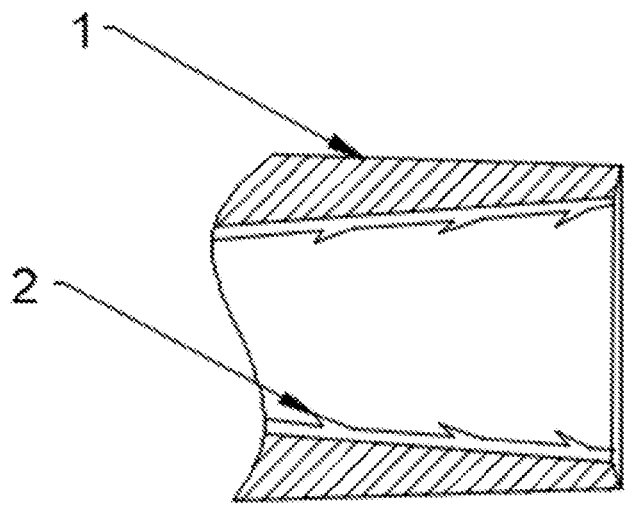
FIG. 3 is a schematic diagram of cross section of the finger sleeve of the present application.

As shown in FIG. 2, based on the implementation of Embodiment 1, this embodiment provides a device for realizing the above-mentioned finger kneading rating method based on intelligent model processing, including:

a finger sleeve 1, which is used to be sleeved on fingers; in this embodiment, as shown in FIG. 3, it is preferable that the finger sleeve is a silicone finger sleeve, and an anti-skid structure 2 is integrally arranged in the finger sleeve to improve the anti-skid property of the finger sleeve.

a piezoelectric converter 3, which is arranged on the finger sleeve, and is used for acquiring and sending finger kneading piezoelectric data meeting the preset pressure value; the network reticular piezoelectric sensing polyvinylidene fluoride (PVDF) screen is used as the piezoelectric transducer 3; during finger kneading, the finger surface is pressed against the reticular piezoelectric sensing PVDF screen to obtain piezoelectric data.

an MCU, which is arranged on the finger sleeve and connected with the piezoelectric converter, and is used for receiving the piezoelectric data meeting the preset pressure value, calculating and processing the piezoelectric data by using a data model, and outputting finger effective data; the model and specifications of MCU are not limited here. MUC is nested in silicone finger sleeve.

a display 4, which is attached to the outer surface of the finger sleeve for receiving and displaying the finger effective data.

a battery 5, which is installed inside the finger sleeve and electrically connected with the piezoelectric converter, MCU and display. Adopt removable and replaceable lithium battery.

After the piezoelectric sensor "senses" the pressure change, the voltage change is transmitted to the MCU, which converts it into a voltage value after MCU operation. According to the piezoelectric conversion result, if the voltage is greater than 0.05 v or other thresholds set according to the project requirements, it is calculated as an effective movement event, such as the touch pressure is greater than 0.05 Pa or other set thresholds are regarded as an effective touch, and it is recorded as an effective finger kneading action, and the duration of these finger kneading movement events is 5 s or other set duration, and finally it is effective.

The final result obtained by "MCU" is displayed on the input display screen, and accumulated in turn. When the longer duration set has expired, the finger kneading movement is terminated.

For the functions and implementation principles of each module/hardware, refer to the descriptions of the foregoing embodiments for details, and details are not repeated here.

Embodiment 3

Furthermore, according to another aspect of the present application, a rating system is also provided, including:
a processor;
a memory, which is used for storing processor executable instructions;
where the processor is configured to implement the finger kneading rating method based on intelligent model processing above when executing the executable instructions.

The rating system of the embodiment includes a processor and a memory for storing executable instructions of the processor. The processor is configured to implement any one of the above-mentioned finger kneading rating methods based on intelligent model processing when executing the executable instructions.

Here it should be pointed out that the number of processors could be one or more. Memory, as a computer readable storage medium, could be used to store software programs, computer executable programs and various modules, so as to perform various functional applications and data processing of the rating system.

The embodiments of the present application have been described above, and the above description is exemplary, not exhaustive, and not limited to the embodiments related to. Without departing from the scope and spirit of the described embodiments, many modifications and changes will be obvious to those of ordinary skill in the technical field.

What is claimed is:

1. A device for realizing a finger kneading rating method based on intelligent model processing, comprising:
    a finger sleeve used to be sleeved on fingers;
    a piezoelectric converter arranged on the finger sleeve to obtain finger kneading piezoelectric data of all finger kneading times in each array, wherein each array is preset and comprises finger kneading times; and
    calculate an average value of obtained finger kneading piezoelectric data of all finger kneading times in each array, and take average values of the arrays as a piezoelectric data set;
    a monitor control unit arranged on the finger sleeve and connected with the piezoelectric converter, and used for receiving the piezoelectric data from the piezoelectric data set, calculating and processing the piezoelectric data by using a data model, and outputting finger effective data;
    a display arranged on the finger sleeve and used for receiving and displaying the finger effective data; and
    a battery arranged on the finger sleeve and electrically connected with the piezoelectric converter, the monitor control unit and the display.

2. The device according to claim 1, wherein the finger sleeve is a silicone finger sleeve.

3. The device according to claim 1, further comprising an anti-slip structure arranged in the finger sleeve.

4. The device according to claim 1, wherein the piezoelectric converter is a reticular piezoelectric sensing polyvinylidene fluoride screen.

\* \* \* \* \*